United States Patent [19]

Hennart

[11] 4,189,475

[45] Feb. 19, 1980

[54] INSECTICIDAL COMPOSITIONS EXHIBITING A SYNERGISTIC EFFECT

[75] Inventor: Claude Hennart, Seraincourt, France

[73] Assignee: Airwick Industries Inc., Carlstadt, N.J.

[21] Appl. No.: 862,079

[22] Filed: Dec. 19, 1977

[30] Foreign Application Priority Data

Dec. 24, 1976 [LU] Luxembourg .......................... 76473

[51] Int. Cl.² .................. A01N 9/02; A01N 9/12; A01N 9/28; A01N 9/36
[52] U.S. Cl. .................................. 424/200; 424/213; 424/275; 424/282; 424/285
[58] Field of Search .................................. 424/200, 213

[56] References Cited

U.S. PATENT DOCUMENTS

| 3,193,452 | 7/1965 | Jäger et al. ............................. 424/300 |
| 3,658,959 | 4/1972 | Inks ......................................... 424/300 |
| 3,919,244 | 11/1975 | Kristinsson ......................... 260/294.8 C |

FOREIGN PATENT DOCUMENTS 537873 5/1955 Belgium .

OTHER PUBLICATIONS

C.A. vol. 83, 1975, 127410c.

*Primary Examiner*—Allen J. Robinson
*Attorney, Agent, or Firm*—Harry Falber

[57] ABSTRACT

An insecticidal composition which contains a combination A of O,O-dimethyl S-[1,2-bis-(ethoxycarbonyl)-ethyl] dithiophosphate with at least one of the insecticides defined under (a) and (a') below:

(a) O,O-dimethyl S-(4-aza-6-chloro-2-oxo-benzoxazol-3-yl)-methyl thiophosphate, and (a') an ortho-substituted phenyl N-methylcarbamate having the following formula:

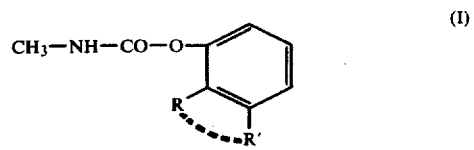

(I)

in which R is an alkyl radical containing 1 to 5 carbon atoms, a propargyloxy radical, a dialkoxymethyl radical in which the alkoxy group contains 1 to 4 carbon atoms, a dioxolanyl radical or a dioxanyl radical, these two latter radicals being unsubstituted or substituted by 1 or 2 methyl groups, and R' is a hydrogen atom, or R and R', together with the two carbon atoms of the benzene ring to which they are attached, form a thiophene ring, a dioxolane ring or dihydrofurane ring, these rings being unsubstituted or substituted by one or two methyl groups.

4 Claims, No Drawings

INSECTICIDAL COMPOSITIONS EXHIBITING A SYNERGISTIC EFFECT

The present invention relates to new insecticidal compositions which are mixtures which exhibit a synergistic effect and comprise two active compounds chosen from amongst O,O-dimethyl S-[1,2-bis-(ethoxycarbonyl)-ethyl] dithiophosphate, hereafter referred to as MALATHION, on the one hand, and an insecticide chosen from amongst O,O-dimethyl S-(4-aza-6-chloro-2-oxo-benzoxazol-3-yl)-methyl thiophosphate, hereafter referred to as AZAMETHIPHOS, and certain ortho-substituted phenyl N-methylcarbamates, on the other hand.

By "mixture having a synergistic effect" there is here understood a combination of two active compounds, the efficacy of which, in terms of its intensity, exceeds the expected sum of the efficacies of each of these active compounds.

Belgian Pat. No. 537,873 describes synergistic mixtures of organic phosphates, such as MALATHION, with various organic carbamates, entirely different from those used in the new mixtures discovered by the Applicant.

French Pat. No. 1,306,384 also describes mixtures of organic phosphates, preferably aromatic phosphates, with organic carbamates which are different from those present in the new compositions according to the invention.

It is known that the synergistic effect of such a combination does not conform to any rule and is completely unforseeable.

The Applicant has now discovered the surprising fact that certain specific mixtures of active compounds possess an insecticidal efficacy which is markedly greater than would be expected from the sum of the individual efficacies.

This phenomenon in particular makes it possible to reduce the use doses of the insecticidal materials, which is of undoubted economic value and is an advantage from the ecological point of view and from the point of view of safety of the users.

The present document thus proposes insecticidal compositions which comprise:

A. A combination of at least two active compounds comprising O,O-dimethyl S-[1,2-bis-(ethoxycarbony)-ethyl] dithiophosphate, also referred to as Malathion, and an insecticide selected from amongst:

a. O,O-dimethyl S-(4aza-6-chloro-2-oxo-benzoxazol-3-yl)methyl thiophosphate, also referred to as Azamethiphos, and a'. An ortho-substituted phenyl N-methylcarbamate which possesses the following formula:

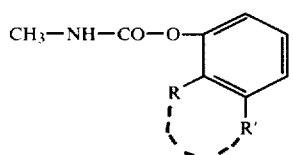

(I)

in which R is an alkyl containing 1 to 5 carbon atoms, a propargyloxy radical, a dialkoxymethyl radical in which the alkoxy group contains 1 to 4 carbon atoms, a dioxolanyl radical or a dioxanyl radical, these two latter radicals being unsubstituted or substituted by 1 or 2 methyl groups, and R' is a hydrogen atom, or R and R', together with the two carbon atoms of the benzene ring to which they are attached, form a thiophene ring, a dioxolane ring or a dihydrofurane ring, these rings being unsubstituted or substituted by one or two methyl groups.

B. Optionally, an adjuvant selected from amongst foodstuffs, surface-active agents, dyes, pigments, stabilisers, solid diluents and liquid diluents which are compatible with the active materials used.

The ortho-substituted phenyl N-methylcarbamate a' can be selected, for example, from amongst the following: ortho-cresyl N-methylcarbamate, 2-ethyl-phenyl N-methylcarbamate, 2-isopropyl-phenyl N-methylcarbamate, 2-tertiary butyl-phenyl N-methylcarbamate, 2-sec.-butyl-phenyl N-methylcarbamate, 2-tertiary amyl-phenyl N-methylcarbamate, 2-propargyloxy-phenyl N-methylcarbamate, 2-dimethoxymethyl-phenyl N-methylcarbamate, 2-diethoxymethyl-phenyl N-methylcarbamate, 2-(1,3-dioxolan-2-yl)-phenyl N-methylcarbamate (also known as DIOXACARB), 2-(4-methyl-1,3-dioxolan-2-yl)-phenyl N-methylcarbamate, 2-(4,5-dimethyl-1,3-dioxolan-2-yl)-phenyl N-methylcarbamate, 2-(1,3-dioxan-2-yl)-phenyl N-methylcarbamate, 2-(4-methyl-1,3-dioxan-2-yl)-phenyl N-methylcarbamate, 2,2-dimethyl-1,3-benzodioxol-4-yl N-methylcarbamate (also known as BENDIOCARB), 2,2-dimethyl-dihydrobenzofuran-7-yl N-methylcarbamate (also known as CARBOFURAN) and benzothien-4-yl N-methylcarbamate (also known as MOBAM).

The ortho-substituted phenyl N-methylcarbamates preferred in the compositions according to the invention are BENDIOCARB and above all DIOXOCARB.

However, the mixtures according to the invention which exhibit the greatest synergistic effect are those which contain a combination A of MALATHION and AZAMETHIPHOS.

The ratio of the active compounds in the combination A is preferably from 0.2 to 5 parts of one per part of the other.

The compositions according to the invention can assume any of the known forms; for example, they can constitute an insecticidal liquid, an aerosol formulation, an insecticidal dusting powder, a wettable powder, an emulsifiable liquid, a bait or a baiting agent. An insecticidal liquid contains, for example, between 0.2 and 20% of the combination A, calculated relative to the weight of the liquid, this proportion being preferably between 0.5 and 10%; the remainder consists of a solvent or solvent mixture which is compatible with the constituents of the combination A and can in particular comprise a saturated hydrocarbon, an aromatic hydrocarbon, a ketone compound and/or an ester of a carboxylic acid.

An aerosol formulation comprises, for example, between 0.2 and 6% of the combination A, calculated relative to the weight of the formulation, this proportion being preferably between 0.5 and 3%; the remainder consists, on the one hand, of a solvent or solvent mixture which is liquid at ambient temperatures and pressures and which can in particular comprise a chlorinated hydrocarbon and/or a saturated hydrocarbon and/or an aromatic hydrocarbon and, on the other hand, a propellant which is gaseous at ambient temperatures and pressures, such as butane, isobutane, propane, dimethyl ether, carbon dioxide, nitrogen, nitrous oxide, trichlorofluoromethane, dichlorodifluoromethane, 1,2-dichloro-1,1,2,2-tetrafluoroethane, tetrafluoromethane and/or octafluorocyclobutane. Preferably, such a formulation contains between 20 and 80% of propellant.

An insecticidal dusting powder comprises, for example, between 0.5 and 10% of the combination A, calculated relative to the weight of the powder, this proportion preferably being between 1 and 5%; the remainder consists of a material which is inert towards the constituents of the combination A and is pulverulent, and consists of or contains a talc, kaolin, a dry clay, a fossil silica, a synthetic silica, a non-fossil natural silica, vermiculite, a magnesium silicate, an aluminum silicate, a calcium phosphate, calcium carbonate, a wood flour, a soya flour and/or a nutshell flour.

A wettable powder comprises, for example, between 1 and 40% of the combination A, calculated relative to the weight of the powder, this proportion being preferably between 2 and 20%; the remainder consists of a material which is inert towards the constituents of the combination A, is pulverulent, is able to absorb the composition completely and can in particular comprise the materials enumerated above in connection with the dusting powder, the wettable powder additionally containing one or more surface-active agents chosen so as to impart to the powder a wettability and a suspendability in water at least equal, for example, to that defined by Standard Specifications SIF/9 R2 and SIF/10 R2 of the World Health Organisation.

An emulsifiable liquid comprises, for example, between 2 and 30% of the combination A, calculated relative to the weight of the liquid, this proportion being preferably between 5 and 20%; the remainder consists of one or more surface-active agents intended to allow good dispersion in water and good stability in emulsion; the remainder may also optionally contain a solvent or solvent mixture which in particular can comprise a saturated hydrocarbon and/or aromatic hydrocarbon and/or a chlorinated hydrocarbon. The proportion of surface-active agent in such an emulsifiable liquid is approximately between 5 and 30%.

An insecticidal bait comprises, for example, between 0.2 and 6% of the combination A calculated relative to the weight of the bait, this proportion being preferably between 1 and 4%; the remainder consists of one or more edible substances such as, in particular, sugars, cereal flours, milk powder, meat meals or fish meals, and flours and starches from tubers; the remainder can furthermore comprise lures and/or absorbent inert fillers and/or binders such as vegetable or mineral oils, colophony, white petroleum jelly or paraffin. A baiting agent comprises, for example, between 2 and 50% of the combination A, calculated relative to the weight of the bait, this proportion being preferably between 10 and 50% if the agent does not comprise a volatile solvent, the remainder then being a diluent such as a vegetable or mineral oil, which can contain a lure for the insects to be destroyed; on the other hand, the said proportion is preferably between 20 and 30% if the agent contains a volatile solvent such as, in particular, methylene chloride, isopropanol, methanol, ethanol, acetone, methyl acetate, dioxane, tetrahydrofurane, ethyl acetate, 2-methoxy-ethanol and 2-methoxy-ethyl acetate; the presence of such a solvent facilitates the distribution of the agent in or on the foodstuff which has to used as a bait.

Each of these forms can advantageously contain a dye, a pigment and/or a stabiliser for the active materials, such as magnesium carbonate, buffer salts having a pH of between 6 and 7, epoxide compounds and fatty monoesters of sorbitane.

A liquid form can optionally be supported on a porous or fibrous material, such as a board or foam rubber or synthetic polymer.

The synergistic effect of the compositions according to the invention is illustrated by the experiments which follow.

EXPERIMENT A

The following compositions A1, A2 and A3 were prepared in aerosol containers (percentages being by weight):

| Composition | A1 | A2 | A3 |
|---|---|---|---|
| Azamethiphos | 2 | — | 1 |
| Malathion | — | 3 | 1.5 |
| Tetrahydrofurane | 2 | 2 | 2 |
| Methylene chloride | 26 | 25 | 25.5 |
| Trichlorofluoromethane | 35 | 35 | 35 |
| Dichlorodifluoromethane | 35 | 35 | 35 |

The contents of each of these containers was distributed, by spraying, over one of the faces of glass plates of size 20×10 cm, at the rate of 800 mg per plate. 5 plates for each composition were prepared in this way; experiments on the insecticidal efficacy were carried out on the second day, and thereafter on the eighth day, following spraying, on insects of the species *Periplaneta americana*, which were placed on the treated face of the plates for one minute and were then placed under observation in ventilated wide-mouthed jars; every 15 minutes, the cumulative proportion of insects which were dead or in dorsal decubitus was recorded (KD%); 10 insects were placed on each plate, representing a total of 50 insects per composition.

The table which follows indicates the results recorded.

| Periods in days | Time in minutes | KD % | | | |
|---|---|---|---|---|---|
| | | A1 | A2 | A3 Expected | A3 Observed |
| 2 | 30 | 0 | 0 | 0 | 4 |
| | 45 | 2 | 18 | 10 | 57 |
| | 60 | 4 | 58 | 31 | 82 |
| | 75 | 4 | 94 | 48 | 92 |
| | 90 | 18 | 98 | 58 | 98 |
| 8 | 30 | 0 | 0 | 0 | 6 |
| | 45 | 8 | 0 | 4 | 16 |
| | 60 | 16 | 4 | 10 | 26 |
| | 75 | 26 | 22 | 24 | 47 |
| | 90 | 34 | 52 | 43 | 53 |

EXPERIMENT B

The procedure of Experiment A was employed, using the following compositions B1, A2 and B3 (percentages being by weight):

| Composition | B1 | A2 | B3 |
|---|---|---|---|
| Dioxacarb | 2 | — | 1 |
| Malathion | — | 3 | 1.5 |
| Tetrahydrofurane | 2 | 2 | 2 |
| Methylene chlorine | 26 | 25 | 25.5 |
| Trichlorofluoromethane | 35 | 35 | 35 |
| Dichlorodifluoromethane | 35 | 35 | 35 |

The tests were carried out on compositions B1 and B3. The table which follows indicates the results in comparison with those noted for composition A2 in Experiment A.

| Periods in days | Time in minutes | B1 | A2 | KD % | |
|---|---|---|---|---|---|
| | | | | B3 | |
| | | | | Expected | Observed |
| | 30 | 14 | 0 | 7 | 44 |
| | 45 | 52 | 18 | 35 | 88 |
| 2 | 60 | 78 | 58 | 68 | 96 |
| | 75 | 84 | 94 | 89 | 100 |
| | 90 | 94 | 98 | 96 | |
| | 30 | 22 | 0 | 11 | 55 |
| | 45 | 84 | 0 | 42 | 96 |
| 8 | 60 | 96 | 4 | 50 | 100 |
| | 75 | 100 | 22 | 61 | |

The results of the preceding experiments show that the efficacy is greater when a mixture of the two compounds is employed than when one or other of these compounds is employed separately.

These experiments related to one species of Orthoptera; of course the compositions according to the invention are equally applicable to the destruction of other species of Orthoptera such as, for example, cockroaches, crickets, grasshoppers and mole-crickets, as well as to other orders of insects such as, for example, the Diptera (flies, Stomoxynae, Culex and Aedes), the Hemiptera (Cimex, aphids and Triatomidae), the Coleoptera (Oryzaephilus, Dermestes, Trogodoran, Attagenus, Tribolium, Cauthocerus, Tenebrio, Sitophilus and Leptinotarsa), the Hymenoptera (Formicidae), the Lepidoptera (Sitotroga and Plodia), the Isoptera (termites) and the Heteroptera.

The experiment which follows shows that the synergistic effect is not exhibited between Malathion and another insecticide. In fact, not only is an absence of synergism between Malathion and Fenitrothion (b) observed, but even an antagonism between these two compounds.

The compound (b) is O,O-dimethyl O-(3-methyl-4-nitrophenyl) thiophosphate.

EXPERIMENT C

The procedure of Experiment A was employed, using the following three compositions D1, A2 and D3 (percentages being by weight):

| Composition | C1 | A2 | C3 |
|---|---|---|---|
| Fenitrothion | 2 | — | 1 |
| Malathion | — | 3 | 1.5 |
| Tetrahydrofurane | 2 | 2 | 2 |
| Methylene chloride | 26 | 25 | 25.5 |
| Trichlorofluoromethane | 35 | 35 | 35 |
| Dichlorodifluoromethane | 35 | 35 | 35 |

The tests were carried out on compositions C1 and C3. The table which follows indicates the results in comparison with those noted for composition A2 in Experiment A.

| Periods in days | Time in minutes | C1 | A2 | KD % | |
|---|---|---|---|---|---|
| | | | | C3 | |
| | | | | Expected | Observed |
| | 30 | 6 | 0 | 3 | 0 |
| | 45 | 18 | 18 | 18 | 0 |
| | 60 | 26 | 58 | 42 | 0 |
| 2 | 75 | 38 | 94 | 66 | 6 |
| | 90 | 46 | 98 | 72 | 22 |
| | 105 | 66 | 100 | 83 | 56 |
| | 30 | 4 | 0 | 2 | 0 |
| | 45 | 16 | 0 | 8 | 0 |
| | 60 | 20 | 4 | 12 | 0 |
| 8 | 75 | 24 | 22 | 23 | 4 |
| | 90 | 32 | 52 | 42 | 6 |
| | 105 | 34 | 78 | 56 | 16 |
| | 120 | 58 | 86 | 72 | 28 |

EXAMPLES 1 to 10
Emulsifiable or non-emulsifiable liquid formulations, and aerosol formulations

| Composition | 1 | 2 | 3 | 4 | 5 | 6 | 7 | 8 | 9 | 10 |
|---|---|---|---|---|---|---|---|---|---|---|
| Malathion | 0.1 | 1 | 5 | 0.1 | 3 | 5 | 0.5 | 2 | 5 | 5 |
| Dioxacarb | 0.1 | 2 | — | — | 2 | — | — | — | — | — |
| Bendiocarb | — | — | — | — | — | — | 1.5 | 4 | — | — |
| Azamethiophos | — | — | 1 | 0.1 | — | 5 | — | — | 10 | 25 |
| Gasoline, 160/240° C. | 9.8 | 8 | — | — | — | — | — | — | — | — |
| Tetralin | — | — | — | 9.5 | — | 9.5 | 78 | — | — | — |
| Xylene | — | — | — | — | 70 | — | — | 64 | 44 | 28 |
| Isopropanol | — | — | — | 4.8 | 4.5 | — | — | — | — | — |
| Tetrahydrofuran | — | — | 10 | — | 20 | — | 4.5 | 10 | 20 | 20 |
| Ethyl acetate | — | — | — | — | — | 80 | — | — | — | — |
| Polyoxyethyleneated nonylphenol[b] | — | — | — | — | — | — | 15 | — | — | — |
| Polyoxyethyleneated tributylphenol[b'] | — | — | — | — | — | — | — | — | — | 20 |
| Sorbitane sesqioleate[c] | — | — | — | — | — | — | — | 20 | — | — |
| Polyethylene glycol monooleate[c'] | — | — | — | — | — | — | — | — | 20 | — |
| Epichlorohydrin | — | — | — | — | 0.2 | 0.5 | — | — | 1 | 2 |
| Yellow dye[d] | — | — | — | — | 0.3 | — | 0.5 | — | — | — |
| Methylene chloride | 35 | 29 | 34 | — | — | — | — | — | — | — |
| Trichlorofluoromethane | — | 25 | 25 | — | — | — | — | — | — | — |
| Dichlorodifluoromethane | 33 | 35 | 25 | — | — | — | — | — | — | — |
| Butane | 22 | — | — | — | — | — | — | — | — | — |

[b]Condensate of four mols of ethylene oxide with one mol of nonylphenol, sold under the trademark "CEMULSOL NPT-14" by the French Company Melle-Bezons.
[b']Condensate of eight mols of ethylene oxide with one mol of tributylphenol, sold under the trademark "SAPOGENAT T-080" by the German Company Farbwerke Hoechst AG of Frankfurt.
[c]Main component of the wetting agent sold under the trademark "ATLACEL C" by the U.S. Company Atlas Chemical Industries of Wilmington (Delaware).
[c']Condensate of five mols of ethylene oxide with one mol of oleic acid, sold under the trademark "CEMULSOL AP" by the French Company Melle-Bezons.
[d]5-Hydroxy-3-methyl-1-phenyl-4-phenylazo-pyrazole (Colour Index No. 12,700, Solvent Yellow 16).

EXAMPLES 11 to 20
Dusting powders and wettable powders

| Composition | 11 | 12 | 13 | 14 | 15 | 16 | 17 | 18 | 19 | 20 |
|---|---|---|---|---|---|---|---|---|---|---|
| Malathion | 0.2 | 1 | 1 | 1 | 4 | 0.2 | 3 | 6 | 10 | 20 |
| Dioxacarb | — | 2 | 1 | — | 6 | — | — | — | — | — |
| Bendiocarbe | — | — | — | — | — | — | — | 4 | — | — |
| Azamethiphos | 0.3 | — | 1 | 4 | — | 0.8 | 2 | — | 10 | 20 |
| Talc | 91 | 95 | — | — | — | — | — | — | — | — |
| Kaolin | — | — | — | 91 | — | 85 | 75 | 58 | 47 | 19 |
| Fossil diatomaceous earth | — | 1.5 | — | — | 8 | — | — | — | 20 | — |
| Synthetic sodium silico- | — | — | — | 2.5 | — | 3 | 6 | 20 | — | 25 |

-continued

EXAMPLES 11 to 20
Dusting powders and wettable powders

| Composition | 11 | 12 | 13 | 14 | 15 | 16 | 17 | 18 | 19 | 20 |
|---|---|---|---|---|---|---|---|---|---|---|
| aluminate | | | | | | | | | | |
| Calcium carbonate | 8.5 | — | — | — | 81 | 3 | 5.5 | — | — | — |
| Soya flour | — | — | 90 | — | — | — | — | — | — | — |
| Sodium salt of the sulphate half-ester of lauryl alcohol oxyethyleneated with 5 mols of ethylene oxide$^e$ | — | — | — | — | — | 3 | — | — | — | — |
| Sorbitan monoleate$^f$ | — | — | — | — | — | — | — | 3 | — | 3 | 3 |
| Triethanolamine lauryl-sulphate$^g$ | — | — | — | — | — | — | — | 3 | — | — |
| Sodium dinaphthylmethane-disulphonate$^f$ | — | — | — | — | — | 5 | 5 | — | 5 | 5 |
| Sodium oxylignin-sulphonate$^f$ | — | — | — | — | — | — | — | 5 | — | — |
| Magnesium carbonate | — | 0.5 | — | — | — | — | — | 3 | 5 | 5 |
| Octyl epoxystearate | — | — | — | 0.5 | — | — | 0.5 | — | — | |
| | | | | | | | | 5 | | |
| | | | | | | | | —3 | | |
| Epoxidised soya oil | — | — | 0.5 | — | 1 | — | — | — | — | 3 |
| Blue pigment$^k$ | — | — | — | 1 | — | — | — | 1 | — | — |

$^f$ Main component of the wetting agent sold under the trademark "SPAN 80" by the U.S. Company Atlas Chemical Industries of Wilmington (Delaware).
$^f$ Main component of the dispersing agent sold under the trademark "SELLASOL TD" by the Applicant Company.
$^f$ Main component of the dispersing agent sold under the trademark "VANISPERSE CB" by the Norwegian Company Borregaard of Sarpsborg.
$^g$ Main component of the wetting agent sold under the trademark "SIPON LT-40" by the French Company SINNOVA.
$^g$ Main component of the wetting agent sold under the trademark "ERIOPON G.O." by the Applicant Company.
$^h$ Pigment manufactured by the Applicant Company, listed in the Colour Index under number 74,160 (Pigment Blue 15).

EXAMPLES 21 to 32
Insecticidal baits

| Composition | 21 | 22$^i$ | 23$^r$ | 24 | 25 | 26 | 27 | 28 | 29 | 30 | 31 | 32 |
|---|---|---|---|---|---|---|---|---|---|---|---|---|
| Malathion | 0.1 | 0.6 | 0.6 | 1 | 1 | 1 | 1 | 1 | 1 | 2 | 3 | 4 |
| Dioxacarb | — | — | 1.2 | 2 | 2 | 2 | — | — | 1 | 2 | — | — |
| MCDMP$^{h'}$ | 0.1 | — | — | — | — | — | 2 | — | 1 | — | — | — |
| Azamethiphos | — | 0.4 | — | — | — | — | — | 2 | — | — | 2 | 2 |
| Meat meal | 74 | — | — | — | 56 | — | 65 | — | 65 | — | 60 | — |
| Fish meal | — | — | 28.8 | 48 | — | 48 | — | 47 | — | 53 | — | 57 |
| Wheat flour | — | — | — | — | 40 | — | — | — | — | — | — | 20 |
| Maize flour | — | — | 17.4 | 29 | — | 48 | — | 29 | — | — | — | — |
| Sucrose | — | 39 | 11.4 | 19 | — | — | 12 | 15 | 15 | — | — | — |
| Wheatgerms | — | — | — | — | — | — | — | — | — | 41 | 25 | — |
| Brewer's yeast | — | — | — | — | — | — | — | 5 | — | — | 5 | — |
| Lactose | — | — | — | — | — | — | 12 | — | — | — | — | 15 |
| Maltose | 25 | — | — | — | — | — | — | — | 15 | — | — | — |
| Magnesium carbonate | — | — | — | — | — | — | 0.5 | — | — | 0.5 | 1 | 0.5 |
| Epoxidised soya oil | — | — | — | — | 0.2 | — | — | — | 0.3 | — | 0.5 | — |
| Potassium sorbate | — | — | 0.6 | 1 | 0.8 | 1 | 1.5 | 1 | — | 1.5 | 1.5 | 0.5 |
| Fossil diatomaceous earth | — | — | — | — | — | — | — | — | — | — | 2 | 1 |
| Cardboard in sheet form | — | 60 | 37 | — | — | — | — | — | — | — | — | — |
| Colophony | — | — | — | — | — | — | 5 | — | — | — | — | — |
| Acrylic resin $^j$ | — | — | 3 | — | — | — | — | — | — | — | — | — |
| Red pigment $^l$ | 0.8 | — | — | — | — | — | 1 | — | 1.7 | — | — | — |

$^{h'}$ Abbreviation denoting 2-dimethoxymethyl-phenyl N-methylcarbamate.
$^i$ A non-sized cellulose cardboard is used, which is first impregnated with a 50% strength aqueous solution of sugar and then dried in an oven; it is then impregnated with a solution containing the active compounds in a volatile solvent, such as methyl acetate, ethyl acetate, methylene chloride, acetone, methanol or tetrahydrofurane; finally, the solvent is evaporated in a ventilated oven.
$^r$ A cardboard of low thickness, made of sized cellulose fibres, is used; the cardboard is coated on one face with a glue comprising the acrylic resin in the form of a 15% strength solution in a 7:10 acetone/methylene chloride mixture, and the remainder of the formulation, as a powder, is stuck on to this face. Finally, the whole is dried.
$^j$ Self-adhesive acrylic resin which has a viscosity, in a 30% strength solution in acetone at 20° C., of between 20,000 and 25,000 centipoises and is sold under the trademark "Solucryl 3068" by the Company Union Chimique Belge of Brussels.
$^l$ Pigment manufactured by the Applicant Company and selected from amongst the following:
Colour Index 15,880 Pigment Red 63
Colour Index 15,865 Pigment Red 48
Colour Index 15,850 Pigment Red 57/59
Colour Index 12,120 Pigment Red 3

EXAMPLES 33 to 42

Agents for an insecticidal bait

| Composition | 33 | 34 | 35 | 36 | 37 | 38 | 39 | 40 | 41 | 42 |
|---|---|---|---|---|---|---|---|---|---|---|
| Malathion | 0.5 | 1 | 4 | 6 | 7 | 15 | 10 | 15 | 10 | 10 |
| Dioxacarb | 1.5 | — | — | 2 | — | 5 | 20 | — | 30 | 20 |
| MCDP[k'] | — | — | — | 2 | — | — | — | — | — | 20 |
| Azamethiphos | — | 1 | 2 | — | 3 | — | — | 15 | — | — |
| White petroleum jelly | — | — | — | — | 40 | 49 | — | 48 | — | 20 |
| Paraffin, 60/62° | — | — | 2 | — | 10 | — | — | — | — | — |
| Colza oil | 20 | 10 | — | — | 9 | — | — | — | — | 9 |
| Papain | — | — | — | — | 30 | — | — | — | — | 20 |
| Cystine | — | — | — | — | — | 30 | — | 20 | — | — |
| Epoxidised soya oil | — | — | — | 0.5 | 0.5 | 1 | 1 | 2 | 1 | 1 |
| Red dye[k] | 0.2 | — | 0.3 | 0.5 | 0.5 | — | — | — | 1 | — |
| Methylene chloride | 77.8 | — | 21.7 | — | — | — | — | 58 | — | — |
| Ethyl acetate | — | 88 | — | — | — | — | — | — | — | — |
| Isopropanol | — | — | 70 | — | — | — | — | — | — | — |
| Methanol | — | — | — | 69 | — | — | 39 | — | — | — |
| Tetrahydrofurane | — | — | — | — | — | — | 30 | — | — | — |
| Dioxane | — | — | — | 20 | — | — | — | — | — | — |

[k] 1-(4-Phenylazo-phenylazo)-2-ethylamino-naphthalene (Colour Index 26,050 - Solvent Red 19) or 1-(2-methoxy-phenylazo)-2-naphthol (Colour Index 12,150 - Solvent Red 1)
[k'] Abbreviation denoting 2-(1,3-dioxan-2-yl)-phenyl N-methylcarbamate.

What is claimed is:

1. An insecticidal composition comprising adjuvants and from about 0.2 to 50%, by weight, of a combination of active ingredients, said combination containing from 0.2 to 5 parts by weight of O,O-dimethyl S-[1,2-bis-(ethoxy-carbonyl)-ethyl] dithiophosphate per part by weight of O,O-dimethyl S-(4-aza-6-chloro-2-oxo-benzoxazol-3-yl)-methyl thiophosphate.

2. A composition according to claim 1, which contains an adjuvant selected from the group consisting of foodstuffs, surface-active agents, dyes, pigments, stabilisers, solid diluents, liquid diluents and propellants compatible with the active compounds used.

3. A composition according to claim 1, which contains a stabiliser for the active compounds selected from the group consisting of magnesium carbonate, buffer salts having a pH of between 6 and 7, epoxide compounds and fatty monoesters of sorbitane.

4. A process for combating harmful insects, which comprises applying to the insects or the infested areas an insecticidally effective amount of a composition according to claim 1.

* * * * *